United States Patent [19]

Sheldon et al.

[11] 4,146,737

[45] Mar. 27, 1979

[54] CHLORINATION OF 3-PHENOXYTOLUENE

[75] Inventors: Roger A. Sheldon; Robert Van Helden, both of Amsterdam, Netherlands

[73] Assignee: Shell Oil Company, Houston, Tex.

[21] Appl. No.: 836,807

[22] Filed: Sep. 26, 1977

[30] Foreign Application Priority Data

Oct. 6, 1976 [GB] United Kingdom ............... 41526/76

[51] Int. Cl.[2] ........................ C07C 43/28; C07C 41/00
[52] U.S. Cl. .................................................. 568/639
[58] Field of Search ................ 260/651 R, 600, 612 R

[56] References Cited

U.S. PATENT DOCUMENTS

| 2,302,228 | 11/1942 | Kharasch et al. | ............ 260/651 R X |
| 3,920,757 | 11/1975 | Watson | ........................ 260/612 R X |

*Primary Examiner*—Bernard Helfin

[57] ABSTRACT

3-Phenoxytoluene is selectively chlorinated at the methyl moiety by treating it with sulfuryl chloride in the presence of a free-radical initiator in a specified manner under specified conditions.

1 Claim, No Drawings

CHLORINATION OF 3-PHENOXYTOLUENE

BACKGROUND OF THE INVENTION

Mixtures of 3-phenoxybenzyl chloride and 3-phenoxybenzal chloride are of interest for the preparation of insecticides: U.S. Pat. No. 4,014,940. It is highly desirable that such mixtures contain a minimum of ring-chlorinated by-products: not only do these by-products represent a loss of the desired products, but in the procedures shown in the patent, and in copending application Ser. No. 762,541 and now U.S. Pat. No. 4,085,147, by which a mixture of 3-phenoxybenzyl chloride and 3-phenoxybenzal chloride is converted to the insecticide, any ring-substituted by-product therein, or by-product(s) derived therefrom, will appear as undesirable contaminant(s) in the insecticide. Once formed, such ring-substituted by-products are very difficult to separate from the mixtures of the benzyl-and benzal chlorides, because of the similarities of their properties to those of the desired products.

Further, unreacted 3-phenoxytoluene also presents similar problems.

It is accordingly desirable to have available a method for converting 3-phenoxytoluene to mixtures of 3-phenoxybenzyl chloride and 3-phenoxybenzal chloride selectively in as high yield as possible.

It has now been found that such results can be attained by treating 3-phenoxytoluene with sulfuryl chloride, in the presence of a free-radical initiator, in a certain manner, under certain conditions.

DESCRIPTION OF THE INVENTION

According to this invention, 3-phenoxytoluene is selectively converted to a mixture of 3-phenoxybenzyl chloride and 3-phenoxybenzal chloride by introducing sulfuryl chloride at a controlled rate into a solution of 3-phenoxytoluene in a chlorinated hydrocarbon solvent containing a free-radical initiator, at a temperature of at least about 50° C., the total amount of sulfuryl chloride employed being from about 1.5 to about 3 moles per mole of the 3-phenoxytoluene.

It has been found that one important factor influencing the formation of ring-chlorinated by-products is the concentration of sulfuryl chloride in the reaction mixture. In particular, high initial concentrations of sulfuryl chloride appear to favor ring-chlorination. It is therefore essential to maintain a relatively low concentration of sulfuryl chloride in the mixture. The sulfuryl chloride preferably is introduced into the reaction mixture at a controlled rate which is essentially the rate at which it reacts with the toluene. This can be readily accomplished by gradually introducing the sulfuryl chloride into the stirred mixture over a period of time. In the usual case, with adequate mixing, this period of time suitably is from one to five hours. To avoid any local high concentration of sulfuryl chloride, the reaction mixture should be thoroughly stirred as the sulfuryl chloride is added. To moderate its effect, the sulfuryl chloride may be, and preferably is, added as a solution in the chlorinated hydrocarbon solvent.

It also has been found that lower temperatures appear to favor ring chlorination, so that the temperature of the mixture must be maintained at 50° C. or above. It appears that temperatures above about 100° C. do not provide any advantage. The toluene solution should be at, and maintained at, the required temperature during addition of the sulfuryl chloride, which also should be at about that temperature.

Suitable solvents are chlorinated hydrocarbons which are inert in the reaction mixture. These may be aromatic or aliphatic in character. Because they tend to be more inert with respect to the sulfuryl chloride, under the reaction conditions, polychloroalkanes, particularly perchloroalkanes, are preferred. Particularly preferred are such solvents having a boiling point (atmospheric pressure) of from about 50° C. to about 100° C., since these permit the treatment of the 3-phenoxytoluene under reflux conditions—a preferred technique for carrying out the treatment.

The treatment is conveniently conducted at atmospheric pressure.

Any of the compounds commonly used for the generation of free radicals can be used as the free-radical initiator. Preferred are azo- and peroxy-compounds, for example, azoisobutyronitrile, benzoyl peroxide, tertiary-butyl perbenzoate, or a peroxydicarbonate such as dimyristyl peroxydicarbonate.

Only a small amount of the initiator is needed—for example, three to ten grams of the initiator per mole of the toluene is generally suitable.

Within limits, the amount of solvent employed does not appear to be critical. However, with relatively concentrated solutions, it appears that the selectivity of the chlorination tends to decrease with increase in the concentration of the toluene. Consequently, it is desirable that the concentration of the toluene in the solvent not exceed about 30% by weight. To conserve solvent and minimize the size of process equipment needed, the concentration of the toluene should be at least 5%, on the same basis.

At least a 50% stoichiometric excess of the sulfuryl chloride, relative to the toluene, is needed to effect conversion of the toluene to the desired degree, but more than a 200% excess is to be avoided to minimize undesirable side reactions, particularly ring chlorination. Optimum results appear to be obtained with about a 70% excess.

Hydrogen chloride is formed as a by-product of the toluene chlorination. To minimize the possibility of its presence causing or catalyzing undesirable side reactions, such as cleavage of the ether linkage of the phenoxytoluene and/or halides derived therefrom, and/or ring chlorination, it is preferred that the hydrogen chloride be removed from the reaction mixture. This can be done by venting the reactor, hydrogen chloride passing therefrom with solvent vapor, solvent inventory being maintained by adding solvent. Also, it can be done by passing an inert gas, such as nitrogen, through the reaction zone to purge the hydrogen chloride therefrom.

The desired product mixture of chlorides can be recovered by evaporating the solvent and vacuum distilling the residue.

Conduct of the process of the invention in particular, exemplary, instances is described in the following examples.

EXAMPLES 1–4

A solution of 10 g of 3-phenoxytoluene (POT) and 0.25 g of azoisobutyronitrile (AIBN) in 50 ml of carbon tetrachloride was heated under reflux while 50 ml of a solution of sulfuryl chloride in carbon tetrachloride was added dropwise at a rate of 14 ml/hour. The mixture then was refluxed to give the indicated reaction time. In some cases, a slow stream of nitrogen was passed through the mixture during the reaction. The product was examined by gas-liquid chromatographic techniques. The results are set out in Table I.

TABLE I

| Example No. | Moles SO$_2$Cl$_2$ / Mole POT | N$_2$ Purge | Reaction Time (Hrs) | POT Conversion (%) | Product Composition (%) | | |
|---|---|---|---|---|---|---|---|
| | | | | | MC[a] | DC[b] | Ring-Cl[c] |
| 1 | 1.5 | Yes | 7 | 91 | 79.2 | 20.2 | 0.6 |
| 2 | 2.0 | Yes | 5 | 97 | 54.4 | 44.8 | 0.8 |
| 3 | 2.5 | No | 6 | 99 | 57.6 | 40.5 | 1.9 |
| 4 | 2.5 | Yes | 5 | 99 | 43.1 | 54.4 | 1.5 |

[a] MC = 3-phenoxybenzyl chloride.
[b] DC = 3-phenoxybenzal chloride.
[c] Mixture of 6-chloro-3-phenoxytoluene, 6-chloro-3-phenoxybenzyl chloride and 6-chloro-3-phenoxybenzal chloride.

EXAMPLES 5 and 6

The procedure of Examples 1–4 was followed, except that all of the sulfuryl chloride (2.5 moles of SO$_2$Cl$_2$/mole of POT) was added at once at the outset. Total reaction time was 5 hours. Conversion of the POT was 100%. In Example 5, a nitrogen purge was used; in Example 6, it was not. The product composition in each case was:

TABLE II

| Example No. | Product Composition (%) | | |
|---|---|---|---|
| | MC | DC | Ring-Cl |
| 5 | 43.5 | 42.0 | 12.1 |
| 6 | 52.3 | 32.4 | 15.5 |

EXAMPLES 7 and 8

The procedure of Examples 1–4 was repeated using benzoyl peroxide, rather than AIBN as initiator. Reaction time: 6 hours. In Example 7, 1.5 moles of SO$_2$Cl$_2$/mole POT; in Example 8, 2.0 moles SO$_2$Cl$_2$/mole POT. Nitrogen purge used in both cases. POT conversion and product composition were:

TABLE III

| Example No. | POT Conversion (%) | Product Composition (%) | | |
|---|---|---|---|---|
| | | MC | DC | Ring-Cl |
| 7 | 88 | 68.2 | 29.6 | 2.2 |
| 8 | 98 | 56.9 | 40.8 | 2.3 |

EXAMPLES 9 and 10

A solution of 46 g of 3-phenoxytoluene and 1.25 g of AIBN in 200 ml of carbon tetrachloride was heated to reflux. Sulfuryl chloride in 100 ml of carbon tetrachloride was added dropwise over a 2.5 hour period to the refluxing mixture. After 3 hours, 0.5 g of AIBN was added and the mixture was refluxed for another 2 hours. The results:

TABLE IV

| Example No. | Moles SO$_2$Cl$_2$ / Mole POT | Conversion POT (%) | Product Composition (%) | | |
|---|---|---|---|---|---|
| | | | MC | DC | Ring-Cl |
| 9 | 1.76 | 99 | 58.8 | 39.9 | 1.2 |
| 10 | 2.0 | 99+ | 39.6 | 59.0 | 1.4 |

We claim:
1. A process for selectively chlorinating the methyl moiety of 3-phenoxytoluene to form a mixture of 3-phenoxybenzyl chloride and 3-phenoxybenzal chloride which comprises introducing sulfuryl chloride into a thoroughly stirred solution of 3-phenoxytoluene in a chlorinated hydrocarbon solvent containing a free radical initiator, at a temperature of at least about 50° C., the sulfuryl chloride being added to said solution at essentially the rate at which it reacts with the 3-phenoxytoluene, with the total amount of sulfuryl chloride employed being from about 1.5 to about 3.0 moles per mole of the 3-phenoxytoluene.

* * * * *